United States Patent

Folko et al.

[11] Patent Number: 5,743,736
[45] Date of Patent: Apr. 28, 1998

[54] SALIVA EJECTOR COMPRISING A NUMBER OF STIFF SECTION MEMBERS

[75] Inventors: Matts Folko, Koping; Christer Albertsson, Eskilstuna, both of Sweden

[73] Assignee: Zirc Company, Buffalo, Minn.

[21] Appl. No.: 640,769
[22] PCT Filed: Nov. 3, 1994
[86] PCT No.: PCT/SE94/01039
 § 371 Date: Aug. 8, 1996
 § 102(e) Date: Aug. 8, 1996
[87] PCT Pub. No.: WO95/13031
 PCT Pub. Date: May 18, 1995

[30] Foreign Application Priority Data

Nov. 8, 1993 [SE] Sweden ............................. 9303675

[51] Int. Cl.⁶ .................................................. A61C 17/06
[52] U.S. Cl. ......................................................... 433/96
[58] Field of Search ............................... 433/96, 140, 31

[56] References Cited

U.S. PATENT DOCUMENTS

| | | |
|---|---|---|
| 950,109 | 2/1910 | Levkowicz ............................. 433/96 |
| 1,471,207 | 10/1923 | Riddle ................................... 433/96 |
| 2,519,595 | 8/1950 | Older ..................................... 433/96 |
| 4,417,874 | 11/1983 | Andersson et al. .................... 433/96 |

FOREIGN PATENT DOCUMENTS

| | | |
|---|---|---|
| 423672 | 1/1978 | Sweden . |
| 415859 | 1/1979 | Sweden . |
| 435338 | 6/1981 | Sweden . |
| 8200764 | 3/1982 | WIPO . |

*Primary Examiner*—John J. Wilson
*Attorney, Agent, or Firm*—Young & Thompson

[57] ABSTRACT

The present invention refers to a disposable saliva ejector (1) for suction of different fluids being present in a dental treatment. The saliva ejector (1) includes a number of stiff section members (10), a connection tube (12) and a suction screen (14). Using a ball-shaped portion in a first end and a corresponding cup-shaped cavity in a second end for connection of the different elements (10, 12 and 14), it is additionally possible by application of a certain minimum force to form the saliva ejector (1) into some desired bent shape before it is inserted into the mouth of a patient to be treated. A saliva ejector is effected which does not contain any further stiffening by metal and therefore a disposable saliva ejector is provided fabricated from only one material for simple destruction and possible recycling of the material.

10 Claims, 4 Drawing Sheets

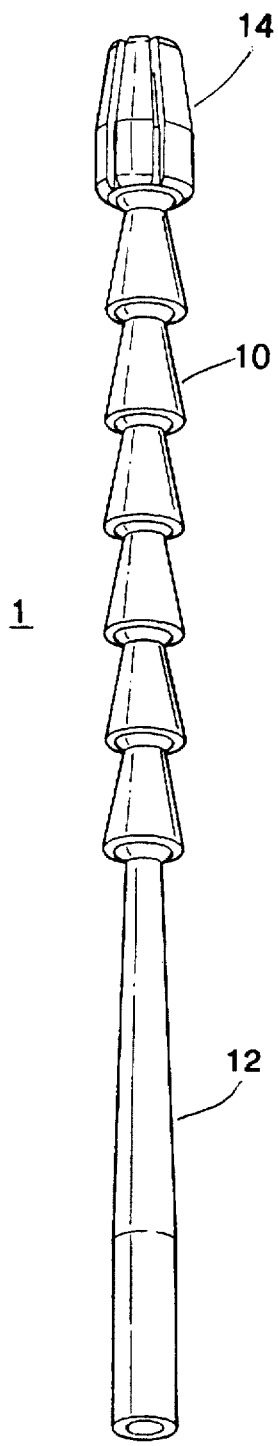
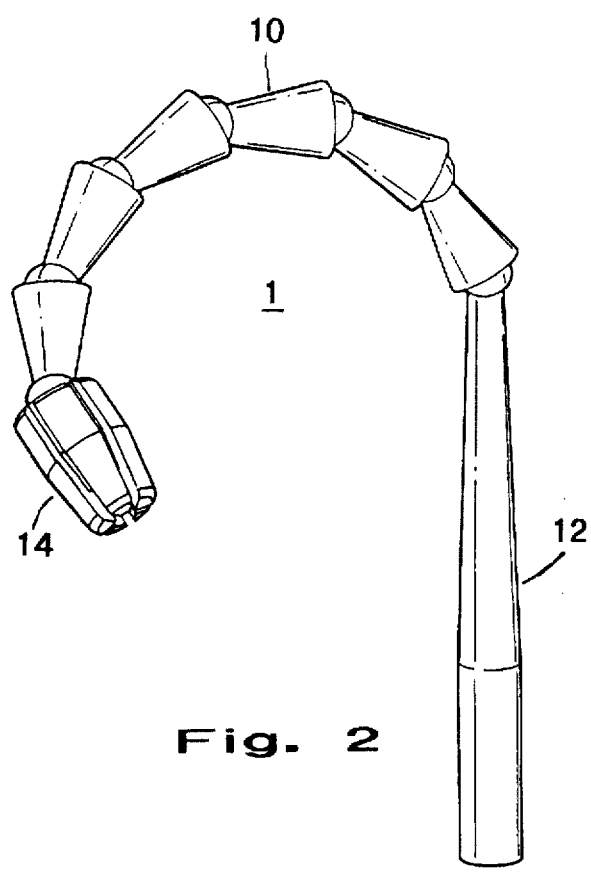
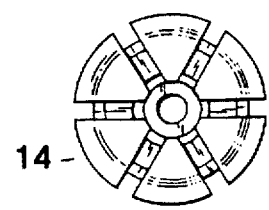
Fig. 1
Fig. 2
Fig. 3

5,743,736

SALIVA EJECTOR COMPRISING A NUMBER OF STIFF SECTION MEMBERS

TECHNICAL FIELD

The present invention relates to an arrangement for a saliva ejector utilized in dental treatment in the oral cavity and more exactly the present invention relates to a saliva ejector comprising a flexible tube without using PVC material and without embedding of metal or corresponding flexible stiffening material.

PRIOR ART

In different treatments within dental care a saliva ejector is usually used to suck saliva and also blood which may be met in smaller surgical operations, as well as different fluids eventually being used for rinsing the oral cavity in connection with the treatment. Such a saliva ejector normally consists of a flexible tube having one or more suction ports in a first end and the other end being connected to a suction tubing.

The most common available saliva ejectors, which are disposable and on 2 yearly basis are made and used in millions of sets by dentists all over the world, have a small hood of PVC, which comprises in part a cage like portion of a larger or smaller length and in part a sleeve portion. The sleeve of the latter portion is slipped onto the suction tubing at its first or the suction port end, such that the cage covers the end of the conduit of the suction tubing. The cage then has the purpose of keeping the soft parts of the oral cavity at a distance from the suction opening of the suction tubing when the saliva ejector with the hood is resting on the lower jaw. The tubing itself is normally formed by some plastic material, in most cases PVC plastic, and provided with an embedded stiffening wire of some other material such as metal.

A typical such arrangement for a saliva ejector is described in the Swedish patent document SE 423 672 filed Jan. 25, 1978. This document discloses a saliva ejector constituting a flexible formable suction tubing having an end portion designed with a row of through holes and being bent double. The tubing itself is made of polyethene and is provided with an embedded wire to obtain the desired plasticity.

Another document SE 415 859 filed Jan. 12, 1979 discloses a corresponding suction tubing which also presents a stiffening metal wire embedded into the plastic material.

In the Swedish patent document SE 435 338 is additionally disclosed a variant wherein the suction tubing consists of a plastic tube where at least one portion of the tube is provided with ridges and intermediate grooves. Preferably the ridges and grooves consist of bellow like folds having sides of different length such that the more narrow sides may be snapped in under the more broad sides upon compressing the bellow like portion. In this manner, the bellow like portion enables a forming of bends on tube consisting of polyethene or polystyrene.

U.S. Pat. No. 2,519,595 further discloses a saliva ejector comprising a Y-formed tube piece which facilitates a double sided saliva ejector, whereby one arm of the Y-formed tube piece presents a ball joint for adjustment of the distance between the two branches of the saliva ejector.

A drawback of saliva ejectors forming disposables according to the state of the art is, in accordance with the examples mentioned above, that the arrangements almost entirely consist of extruded PVC plastic having an imbedded metal wire. In this connection problems arise since the plastic is not simply recoverable, which is an environmental demand growing substantially stronger. Simultaneously the use of the economically cheaper PVC plastic implies further drawbacks as seen from the environmental point of view.

Therefore there is a requirement of a disposable arrangement, cheap in price, in form of a saliva ejector which in part may be produced from a more environmentally friendly material than previously, which at the same time does not contain any metal obstructing recycling of the material, and which exhibits desired flexible bending qualities and yet maintains a defined stiffness upon forming after the appearance of the oral cavity. The shape is maintained also at stresses which may be created when the arrangement is resting against the jaw of a patient.

DESCRIPTION OF THE INVENTION

In accordance with the present invention a disposable saliva ejector is provided which is constructed of only one kind of material which signifies simply recoverable material at the same time as a more environmentally friendly material is possible to be utilized.

According to a first object of the present invention a disposable saliva ejector is provided comprising a suction screen and a number of hollow stiff members made of a suitable stiff material and preferably linked via a corresponding number of ball joints having a high surface accuracy.

According to a second object of the present invention a disposable saliva ejector is provided which is flexible and formable to be able to be fit in a suitable way into the oral cavity of a patient, whereby under moderate stress the arrangement will maintain a bent shape given by the user.

According to a third object of the present invention each member connection presents such a stiffness, that a certain minimum force has to be exerted to change the angle between two individual members.

According to a fourth object of the present invention each member part is made of a material which from the environmental point of view has good qualities, for instance polypropylene or some type of starch product.

DESCRIPTION OF THE DRAWINGS

The invention will be described by means of an illustrative embodiment by means of the attached drawings in which like reference numerals indicate same or like members, and in which:

FIG. 1 is a side view of an embodiment of a saliva ejector according to the present invention having a straight assembled tubing element provided with a suction screen;

FIG. 2 is a tubing provided with a suction screen according to FIG. 1, the tubing according to the present invention having been bent to a certain given shape;

FIG. 3 is a front view of an embodiment of the suction screen;

FIG. 6b is a view along the cross section I—I of the suction screen according to FIG. 6a.

AN ILLUSTRATIVE EMBODIMENT

Figure 4:
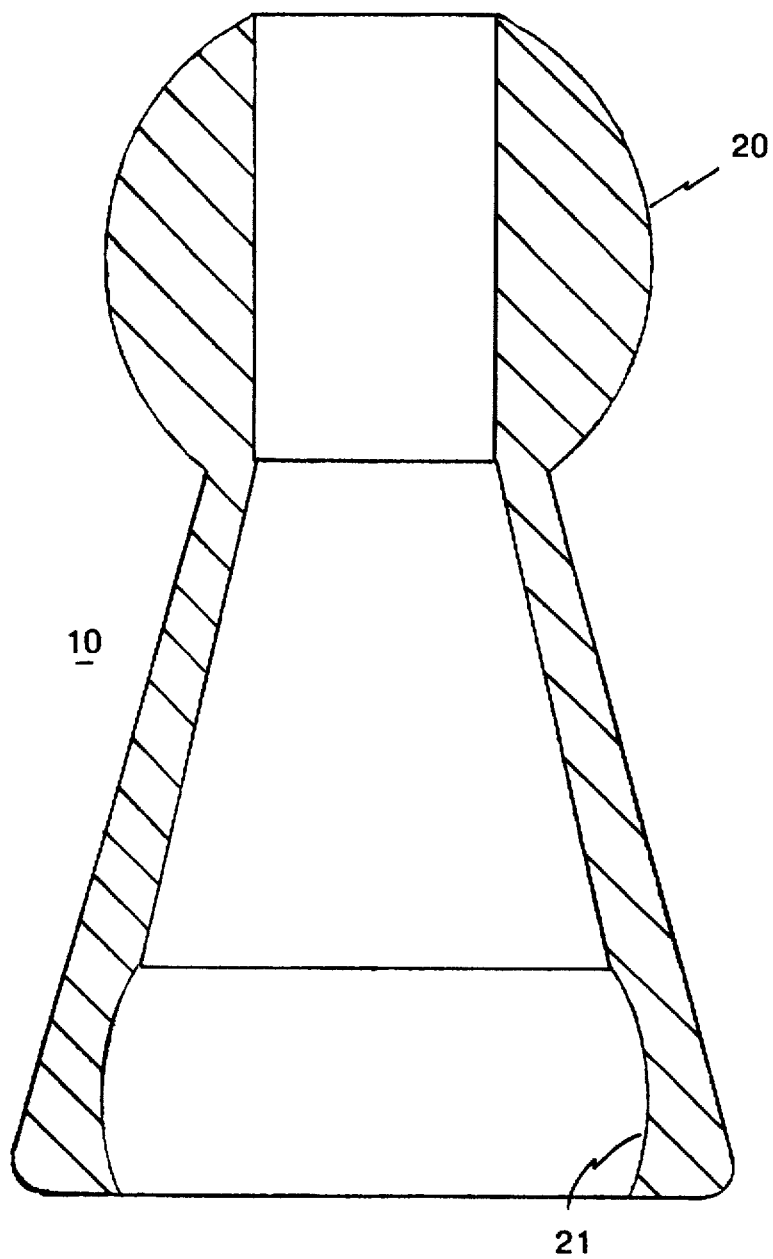
FIG. 4 is a cross section view of an embodiment of a section member according to the present invention.

FIG. 1 illustrates an illustrative preferred embodiment according to the present invention of a saliva ejector referenced by 1. The saliva ejector 1 comprises a number of stiff hollow section members 10, a hollow connection tube 12 and a suction screen 14 having suction ports. In a sterile pack the saliva ejector forms, according to FIG. 1, a straight hollow tube. By means of the connections between the separate parts 10, 12 and 14 it is additionally possible by applying a certain minimum force to form the saliva ejector 1 to some desired bent shape, for instance as shown in FIG. 2, before it is inserted into the mouth of a patient, which is to be treated by a dentist, a dental hygienist, a prophylaxis nurse or the like.

Figure 5A:
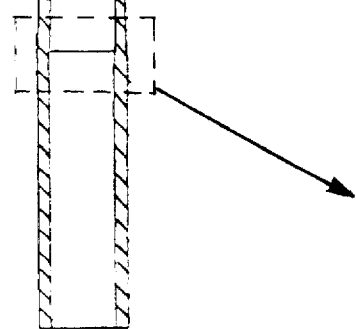
FIG. 5a is a cross section view of an embodiment of a connection tube according to the present invention.

The saliva ejector is shaped in a suitable way to accommodate the oral cavity of the patient such that the suction screen, further shown in FIG. 3, finds a suitable positioning for the current treatment within the oral cavity. In FIG. 5 is demonstrated in a preferred embodiment a stiff section member 10, which is hollow and in a first end exhibits a ball-shaped portion 20 and in a second end exhibits a cup-shaped cavity 21 exactly corresponding to the ball-shaped portion 20 of the first end. The cup-shaped cavity 21 has such a length, that its lower opening in FIG. 4 is slightly less in diameter than the diameter of the ball-shaped portion 20. This means that, when two section members 10 are pressed together with a ball-shaped portion 20 against a cup-shaped cavity 21, the section members will snap into one another and then be locked. In the preferred embodiment only the friction of the snap-in is utilized as a holding and retaining force, while in another embodiment (not shown) it is also possible to use specific clips for the locking of the section members to each other. Additionally in the preferred embodiment the section members 10 are made with a high grade of surface accuracy, whereby the outer diameter of the ball-shaped portion 10 is slightly larger than the available inner maximum diameter of the cup-shaped cavity 21, which thereby creates a suitable friction between the parts. Thus, it is possible by applying a certain force to angle the section members 10 in relation to each other, this slanting angle between the section members 10 being then afterwards in principle maintained. This friction between two members may further if desired simply be increased by providing the surface with a fine pattern, preferably on the ball-shaped portion 20. The through hole of the section member 10 has such a design that when the angle between two section members 10 is at maximum an unlimited internal conduit through the members is obtained. The maximum obtainable angle in any plane between two section members in the embodiment is slightly over 30°. By means of 6 section members a 180° bend of the arrangement in a given plane can be achieved without further ado. Of course it is simple by addition of further section members to achieve a larger total arrangement bend or by further modification of the lower snap-in edge of the cup-shaped cavity 21, which in the illustrative embodiment constitutes a limiting factor of the maximum angling obtained while still maintaining sufficient locking of the members to each other.

Figure 5B:
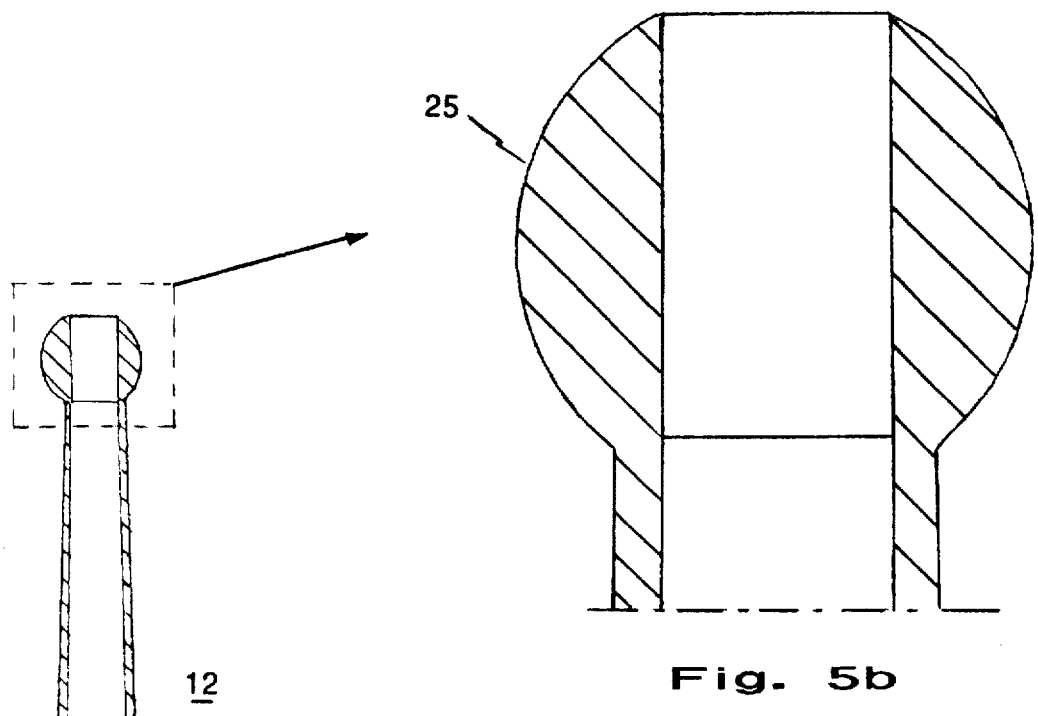
FIG. 5b is an enlarged portion of a first end of the connection tube of FIG. 5a having a ball-shaped part.
Figure 5C:
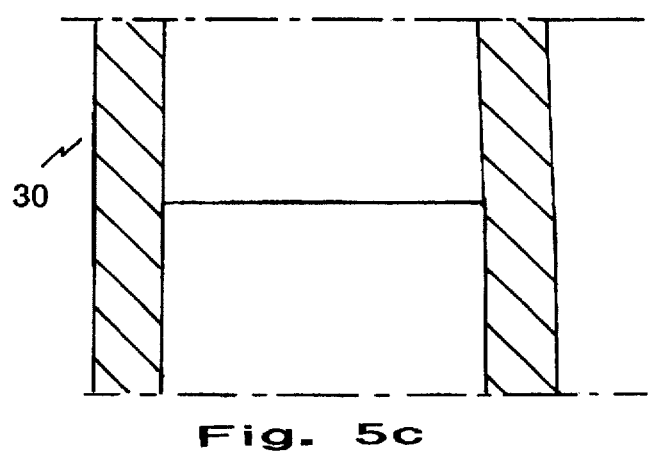
FIG. 5c is an enlarged portion of a second end for connection of the connection tube of FIG. 5a to a tubing.

By assembling a number of section members 10, e.g. six units according to FIG. 1, a saliva ejector 1 is obtained having a tube portion flexible in all directions. At the lower end of the saliva ejector there is a connection tube 12 for connection to a suitable vacuum suction tubing. The connection tube 12, which like the section member has an intercommunication conduit channel, is additionally shown in FIGS. 5a, 5b and 5c. In FIG. 5b is shown an enlargement of one end of the connection tube for connection to a section member 10 and having a corresponding ball-shaped portion 25, all together made as the ball-shaped portion 20 of a section member 10, for snap-in into the cup-shaped cavity 21 of a section member 10. In FIG. 5c is shown an enlarged cross section of the connection tube at a position where this transfers into a fully straight tube 30 for connection to a suitable vacuum tubing. In a corresponding second embodiment (not shown) the connection tube 12 has in its first end a cup-shaped cavity instead of a ball-shaped portion.

Figure 6A:
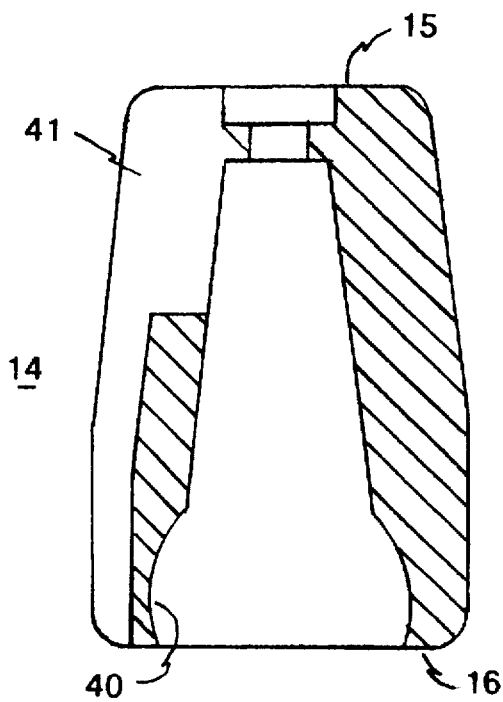
FIG. 6a is a view of an embodiment of a suction screen having an indication of a cut I—I therethrough.
Figure 6B:
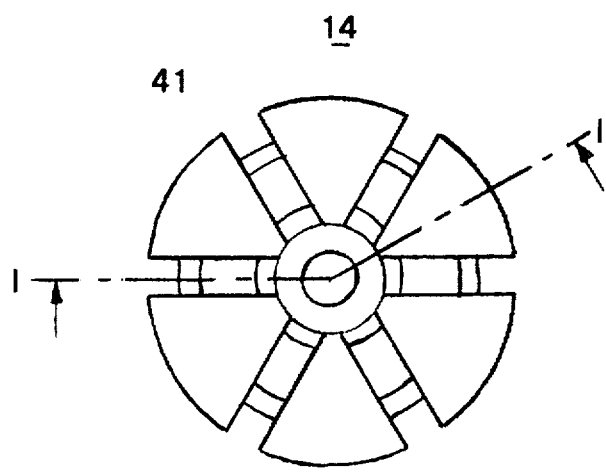

Finally in FIGS. 6a and 6b is shown an embodiment of the suction screen 14, where FIG. 6b is showing a cross section of the suction screen of FIG. 6a along a slanted plane I—I indicated in FIG. 6a. The suction screen in this embodiment is made having 6 slots 41 which in an upper end 15 are in connection with its intercommunication conduit channel. From FIG. 6b is evident that the suction screen in a lower end 16 is made with a corresponding cup-shaped cavity 40, which in the same manner as at the section members 10 corresponds to a ball-shaped portion 20, whereby the suction screen 14 may be snapped onto the tube formed by a number of section members 10 and a connection tube 12 to together form the saliva ejector 1. Corresponding to a second embodiment (not shown) the suction screen is provided with a ball-shaped portion in a lower end to be able to connect to section members 10 connected to a connection tube having a cup-shaped upper end instead of the ball-shaped portion demonstrated in FIG. 5b. The respective members 10, 12 and 14 are made of a material which gives appropriate stiffness and surface structure, e.g., polypropylene or, even more appropriate, by an unalloyed starch product which consequently is even better from the destruction point of view. By means of this connection of the connection tube 12, the section members 10 and the suction screen 14 a saliva ejector 1 is accomplished which does not have to contain any metallic stiffening and thereby offers a more simple destruction or eventual recycling of the material. At the same time the saliva ejector according to the invention offers in principle the same flexibility as a saliva ejector according to prior art having for instance an embedded metal wire in PVC plastic, which material from an environmental point of view today is desired to be avoided.

We claim:

1. A saliva ejector comprising a disposable arrangement in dental treatment for suction of fluids out of the oral cavity of a patient to be treated, including a tubing having a suction screen, said tubing being intended to be inserted into the oral cavity of a patient, said tubing comprising a plurality of stiff hollow section members (10) adjacent of which are fixed to each other to form a plurality of hollow connections that can be turned, a continuous conduit channel in said tubing being formed by said plurality of stiff hollow section members (10) and said plurality of hollow connections, the plurality of stiff hollow section members at each hollow connection of said plurality of hollow connections being turnable to achieve an optional conduit form being able to be adapted to the oral cavity of a patient to be treated.

2. A saliva ejector comprising a disposable arrangement in dental treatment for suction of fluids out of the oral cavity of a patient to be treated, including a tubing having a suction screen, said tubing being intended to be inserted into the oral cavity of a patient, said tubing comprising a number of stiff hollow section members (10) being fixed to each other to form a hollow connection that can be turned, such that a continuous conduit channel is formed in said tubing composed of a number of said stiff hollow section members (10), whereby said tubing by turning of the stiff hollow section members in each hollow connection that can be turned will achieve an optional conduit form being able to be adapted into the oral cavity of a patient to be treated, each stiff hollow section member (10) in a first end having a ball-shape (20) and each stiff hollow section member (10) in a second end having a cup-shaped cavity (21) exactly corresponding to the ball-shape of said first end, two members being able to be snapped into each other to form a bendable tubing having a maintained continuous conduit channel through said bendable tubing and whereby the complete device is constructed of a number of connected stiff hollow section members.

3. The saliva ejector according to claim 2, wherein one end of said bendable tubing is connected to a suction screen (14) and another end of said bendable tubing is connected to a hollow connection tube (12), said suction screen and said hollow connection tube each having an end which mates with an end of said bendable tubing, wherein by assembling said bendable tubing, said suction screen and said connection tube, a saliva ejector device (1) is formed having a continuous conduit channel intended to be fixed to a suction tubing.

4. The saliva ejector according to claim 3 wherein maintaining of the connection between an end having a ball-shape (20, 25) and an end having a cup-shaped cavity (21, 40) is effected by friction.

5. The saliva elector according to claim 3, wherein maintaining of the connection between an end having a ball-shape (20, 25) and an end having a cup-shaped cavity (21, 40) is effected by a locking device.

6. The saliva ejector of claim 5 wherein said locking device is a clip.

7. The saliva elector according to claim 2, wherein each section member (10) as well as said connection tube (12) and said suction screen (14) is molded in only one environmentally friendly material being prone to be recycled.

8. The saliva ejector of claim 7 wherein said material is polypropylene.

9. The saliva ejector according to claim 2, wherein each section member (10) as well as said connection tube (12) and said suction screen (14) is molded from a starch product material being environmentally friendly and easily destructible in a natural way.

10. A saliva ejector, comprising a plurality of stiff hollow section members joined end-to-end at a plurality of respective joints to form a length of tubing extending from one tubing end to an opposite tubing end, each respective joint of said plurality of respective joints pivotally coupling together adjacent stiff hollow section members of said plurality of stiff hollow section members, each joint of said plurality of joints being hollow and forming a continuous conduit channel from said one tubing end to said opposite tubing end.

* * * * *